(12) United States Patent
Taicher et al.

(10) Patent No.: US 6,344,744 B2
(45) Date of Patent: *Feb. 5, 2002

(54) MULTIPLE FREQUENCY METHOD FOR NUCLEAR MAGNETIC RESONANCE LONGITUDINAL RELAXATION MEASUREMENT AND PULSING SEQUENCE FOR POWER USE OPTIMIZATION

(75) Inventors: Gersh Zvi Taicher; Arcady Reiderman, both of Houston, TX (US)

(73) Assignee: Baker Hughes Incorporated, Houston, TX (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/514,724

(22) Filed: Feb. 28, 2000

Related U.S. Application Data

(62) Division of application No. 08/942,123, filed on Oct. 1, 1997, now Pat. No. 6,049,205.

(51) Int. Cl.[7] .................................................. G01V 3/00
(52) U.S. Cl. ........................ 324/303; 324/300; 324/318
(58) Field of Search ................................ 324/303, 300, 324/306, 307, 309, 318

(56) References Cited

U.S. PATENT DOCUMENTS

| 4,832,037 A | 5/1989 | Granot | 128/653 |
|---|---|---|---|
| 4,933,638 A | 6/1990 | Kenyon et al. | 324/303 |
| 5,055,787 A | 10/1991 | Kleinberg et al. | 324/303 |
| 5,055,788 A | 10/1991 | Kleinberg et al. | 324/303 |
| 5,712,566 A | 1/1998 | Taicher et al. | 324/303 |
| 6,051,973 A | * 4/2000 | Prammer | 324/303 |
| 6,084,404 A | * 7/2000 | Chen et al. | 324/303 |

OTHER PUBLICATIONS

Eiichi Fukushima; *Experimental Pulse NMR A Nuts and Bolts Approach*, 1981, Addison–Wesley Publishing Company, Inc. pp. 168–176.

* cited by examiner

Primary Examiner—Jay Patidar
Assistant Examiner—Brij B. Shrivastav
(74) Attorney, Agent, or Firm—Madan, Mossman & Sriram, P.C.

(57) ABSTRACT

A method for determining nuclear magnetic resonance longitudinal relaxation time of a medium. The method includes magnetically polarizing nuclei in the medium along a static magnetic field, momentarily inverting the magnetic polarization of the nuclei within each one of a plurality of different spatial volumes within the medium, transversely magnetizing the nuclei in each one of the spatial volumes after an individual recovery time corresponding to each one of the spatial volumes, and measuring an amplitude of a magnetic resonance signal from each one of the spatial volumes.

5 Claims, 5 Drawing Sheets ing within earth formations surrounding a wellbore. The
MULTIPLE FREQUENCY METHOD FOR NUCLEAR MAGNETIC RESONANCE LONGITUDINAL RELAXATION MEASUREMENT AND PULSING SEQUENCE FOR POWER USE OPTIMIZATION This application is a divisional of application Ser. No. 08/942,123 filed Oct. 1, 1997 now U.S. Pat. No. 6,049,205.

BACKGROUND OF THE INVENTION

1. Field of the Invention

The invention is related to the field of nuclear magnetic resonance ("NMR") sensing apparatus, methods and measuring techniques. More specifically, the invention is related to NMR well logging apparatus and methods for NMR sensing within earth formations surrounding a wellbore. The invention also relates to methods for using NMR measurements to determine petrophysical properties of the earth formations surrounding the wellbore.

2. Description of the Related Art

The description of the background of this invention, and the description of the invention itself are approached in the context of well logging because well logging is a well known application of NMR measurement techniques. It is to be explicitly understood that the invention is not limited to the field of well logging.

An apparatus described in U.S. Pat. No. 4,710,713 issued to Taicher et al is typical of NMR instruments used to measure certain petrophysical properties of earth formations from within a wellbore drilled through the earth formations. NMR well logging instruments such as the one disclosed by Taicher et al typically include a magnet for polarizing nuclei in the earth formations surrounding the wellbore along a static magnetic field, and at least one antenna for transmitting radio frequency ("RF") energy pulses into the formations. The RF pulses reorient the spin axes of certain nuclei in the earth formations in a predetermined direction. As the spin axes precessionally rotate and reorient themselves into alignment with the static magnetic field, they emit RF energy which can be detected by the antenna. The magnitude of the RF energy emitted by the precessing nuclei, and the rate at which the magnitude changes, are related to certain petrophysical properties of interest in the earth formations.

There are several principal operating parameters in NMR well logging which should be optimized for efficient operation of an NMR well logging instrument. These parameters include the logging speed (speed of motion of the instrument along the wellbore), the average and the peak power supplied to the instrument and transmitted as RF pulses, and the signal-to-noise ratio ("SNR"). Other parameters of interest include the vertical resolution of the instrument and the radial depth of investigation of the measurements made by the instrument within the formations surrounding the wellbore. The last two of these parameters are primarily determined by the antenna and magnet configurations of the NMR logging instrument. Improvements to these two parameters are the subject of numerous patents and other publications. Providing more flexibility in the instrument's peak power requirements, and limitations on the logging speed necessitated by the physics of NMR measurement have been more difficult to overcome.

A property of NMR measurements made in porous media such as earth formations is that there is typically a significant difference between the longitudinal relaxation time ("$T_1$") distribution and the transverse relaxation time ("$T_2$") distribution of fluids filling the pore spaces of the porous medium. For example, light hydrocarbons and natural gas, as commonly are present in the pore spaces of some earth formations, may have $T_1$ relaxation times as long as several seconds, while the $T_2$ relaxation times may be only about $\frac{1}{1000}$ that amount. This aspect of NMR well logging is due primarily to the effect of diffusion occurring within static magnetic field amplitude gradients. These amplitude gradients are mainly internal to the pore spaces of the earth formations, and are caused by differences in magnetic susceptibility between the solid portion of the earth formation (referred to as the rock "matrix") and the fluid filling the pore spaces.

In order to perform precise NMR measurements on any medium, including earth formations, the nuclei of the material should be polarized by the static magnetic field for about 5 times the longest $T_1$ relaxation time of any individual component within the material. This is generally not the case for well logging NMR measurements, since some formation components, as previously explained, may have $T_1$ relaxation times as long as several seconds (requiring a polarization time of as long as about 30 seconds). This is such a long polarization time as to make impracticable having enough polarization time at commercially acceptable logging speeds. As the instrument moves along the wellbore, the earth formations which are subject to the static magnetic field induced by the instrument are constantly changing. See for example, *An Experimental Investigation of Methane in Rock Materials* C. Straley, SPWLA Logging Symposium Transactions, paper AA (1997).

As a result of logging speed considerations a polarization time of 8 to 10 seconds has become more common for many NMR well logging procedures, including those used for natural gas detection. See for example, *Selection of Optimal Acquisition Parameters for MRIL Logs*, R. Akkurt et al, The Log Analyst, Vol. 36, No. 6, pp. 43–52 (1996).

Typical NMR well logging measurement procedures include transmission of a series of RF energy pulses in a Carr-Purcell-Meiboom-Gill ("CPMG") pulse sequence. For well logging instruments known in the art, the CPMG pulse sequences are about 0.5 to 1 seconds in total duration, depending on the number of individual pulses and the time span ("TE") between the individual RF pulses. Each series of CPMG pulses can be referred to as a "measurement set".

In the typical NMR well logging procedure only about 5 to 10 percent of the total amount of time in between each NMR measurement set is used for RF power transmission of the CPMG pulse sequence. The remaining 90 to 95 percent of the time is used for polarizing the earth formations along the static magnetic field. Further, more than half of the total amount of time within any of the CPMG sequences actually takes place between individual RF pulses, rather than during actual transmission of RF power. As a result of the small fractional amount of RF transmission time in the typical NMR measurement sequence, the RF power transmitting components in the well logging instrument are used inefficiently on a time basis. In well logging applications this inefficiency can be detrimental to the overall ability to obtain accurate NMR measurements, because the amount of electrical power which can reasonably be supplied to the NMR logging instrument (some of which, of course, is used to generate the RF pulses for the NMR measurements) is limited by the power carrying capability of an electrical cable which is used to move the logging instrument through the wellbore.

Several methods are known in the art for dealing with the problem of non-transmitting time in an NMR measurement set. The first method assumes a known, fixed relationship between $T_1$ and $T_2$, as suggested for example, in *Processing of Data from an NMR Logging Tool,* R. Freedman et al, Society of Petroleum Engineers paper no. 30560 (1995). Based on the assumption of a fixed relationship between $T_1$ and $T_2$, the waiting (repolarization) time between individual CPMG measurement sequences is shortened and the measurement results are adjusted using the values of $T_2$, measured during the CPMG sequences. Disadvantages of this method are described, for example in, *Selection of Optimal Acquisition Parameters for MRIL Logs,* R. Akkurt et al The Log Analyst, vol. 36, no. 6. pp. 43–52 (1996). These disadvantages can be summarized as follows. First, the relationship between $T_1$ and $T_2$ is not a fixed one, and in fact can vary over a wide range, making any adjustment to the purported $T_1$ measurement based on the $T_2$ measurements inaccurate at best. Second, in porous media $T_1$ and $T_2$ are distributions rather than single values. It has proven difficult to "adjust" $T_1$ distributions based on distributions of $T_2$ values.

Another method known in the art for increasing the power efficiency of an NMR well logging instrument is described, for example in, *Improved Log Quality with a Dual-Frequency Pulsed NMR Tool,* R. N. Chandler et al, Society of Petroleum Engineers paper no. 28365 (1994). The Chandler et al reference describes using large downhole capacitors to store electrical energy during the waiting (repolarization) time and then using high peak-power during application of the RF pulses in the CPMG sequences to improve the signal-to-noise ratio ("SNR"). There are several disadvantages to the method described in the Chandler et al reference. First, it is very expensive to have large capacitors in a well logging instrument, which must be able to operate at high temperature (generally in excess of 350° F.). Second, using high peak RF power to improve SNR involves complicated and expensive transmitter switching circuits. The switching circuit design problem is only made worse by the requirement that the well logging instrument be able to withstand 350° F. or more. Using high peak power is also not very effective for the purpose of improving SNR because the SNR increases only as the fourth root of the increase in the peak RF pulse power.

Another NMR logging apparatus, known as the Combinable Magnetic Resonance ("CMR") logging tool, is described in U.S. Pat. No. 5,432,446 issued to MacInnis et al. The CMR logging tool includes permanent magnets arranged to induce a magnetic field at two different lateral distances along the wellbore and at two different radial depths of investigation within the earth formation. Each depth of investigation has substantially zero magnetic field amplitude gradient within a predetermined sensitive volume. The objective of apparatus disclosed in the MacInnis et al '446 patent is to compare the output indications from the first and the second sensitive volumes to determine the effects of borehole fluid "invasion" on the NMR measurements. A drawback to the CMR tool, however, is that both its sensitive volumes are only about 0.8 cm away from the tool surface and extend only to about 2.5 cm radially outward from the tool surface into the earth formation. Measurements made by the CMR tool are subject to large error caused by, among other things, roughness in the wall of the wellbore, by deposits of the solid phase of the drilling mud (called "mudcake") onto the wall of the wellbore in any substantial thickness, and by the fluid content of the formation in the invaded zone.

In NMR well logging measuring techniques, reducing the so-called "dead time" (the time between an initial 90 degree RF pulse and a first one of the 180 degree rephasing pulses in the CPMG sequence) during which no spin-echo measurements are made due to "ringing" of the antenna in the static magnetic field) is important in order to be able to resolve the presence of earth formation components having very short $T_2$ times. As the dead time is reduced, it becomes necessary in a CPMG pulse sequence to reduce the amount of time ("TE") between individual 180 degree rephasing pulses in the CPMG sequence. Some devices, such as one described in, *Measurement of Total NMR Porosity Adds New Value to NMR Logging,* R. Freedman et al, SPWLA Logging Symposium Transactions, paper OO (1997), have achieved a time-to-first-echo (and subsequent TE) of as short as 0.2 milliseconds (msec). Since the expected $T_2$ distribution of typical earth formations extends to one second or more, however, a CPMG measurement sequence of at least 1 sec total length is required to measure the petrophysical properties of typical earth formations. The result of the combination of the need to measure very short and very long $T_2$ relaxation time components results in an CPMG measurement sequence including 8,000 or more echoes ("echo train") using instruments such as the CMR.

Most petrophysical parameters of interest such as irreducible water saturation, fractional volume of movable ("free") fluid, permeability, etc. are based on only one differentiation between "short" (defined as between 0 and about 33 msec) and "long" (defined as more than about 33 msec) parts of the $T_2$ distribution. Assuming the CPMG pulse sequence (and resulting "echo train") is about 1 sec in duration, only about 3 percent of the total duration of the echo train is substantially sensitive to components of the earth formation having short $T_2$ values, as compared to about 97 percent of the echo train being substantially sensitive to components of the earth formation having long $T_2$ values. The nature of the typical echo train therefore results in stable, precise values for parameters such as the fractional volume of free fluid ("FFI"), but can result in unsatisfactory stability and precision in the values determined for other petrophysical properties such as the irreducible water saturation ("BVI"). See for example, *Improved Log Quality with a Dual-Frequency Pulsed NMR Tool,* R. N. Chandler et al, Society of Petroleum Engineers paper no. 28365 (1994).

Because the nature of the relationship between petrophysical properties of interest and certain NMR properties is at best uncertain, it is desirable to be able to measure the longitudinal relaxation time $T_1$ of the earth formations. In NMR well logging measuring techniques, however, $T_1$ measurement has not proven to be practical using the NMR logging apparatus and techniques known in the art. Even if only low accuracy were required, the most the efficient methods of measuring $T_1$ would require at least several seconds in between individual measurement sets to enable the nuclei in the earth formations to repolarize along the static magnetic field. Historically, most laboratory and all field measurements of the petrophysical properties of earth formations were limited to measurements of $T_1$. Based on these results, relationships between the petrophysical properties and the relaxation time $T_1$ were established. As a matter of practical necessity, however, most commercial applications of NMR measurement to well longing substitute the $T_1$ relaxation time by measurements of the $T_2$ relaxation time. In most cases, however, the direct substitution of $T_1$ by $T_2$ for petrophysical interpretation cannot be substantiated. The principal reason for the lack of direct ability to substitute $T_1$ for $T_2$, is that $T_2$ is often affected by molecular diffusion within the internal magnetic field gradients present in the pore spaces of earth formations. These internal gradients are caused by differences in magnetic susceptibility, in the presence of the static magnetic field imparted by the NMR instrument, between the solid portion of the earth formations (the rock "matrix") and the fluid in the pore spaces. Smaller size pore spaces generally have larger internal magnetic field gradients than do larger pore spaces, therefore any correlation between pore size and $T_1$ distribution cannot be directly related to a correlation between pore size and $T_2$ distribution.

A method for increasing the time efficiency of NMR pulsing sequences is described in U.S. Pat. No. 4,832,037 issued to Granot. The method described in the Granot '037 patent includes applying a static magnetic field to materials to be analyzed, momentarily applying a gradient field to the materials to be analyzed and applying an RF pulse to an antenna at a first frequency to transversely polarize the nuclei of the material within a specific geometric region. The specific geometric region is the location at which the total magnetic field strength, which is the sum of the static field and the gradient field, corresponds to the Larmor frequency of the polarized nuclei within the specific geometric region. After the gradient field is switched off, the free induction decay ("FID") signal is measured and spectrally analyzed. During a waiting time, generally about equal to $T_1$, between successive magnetic resonance experiments in the same specific geometric region, additional gradient pulses and RF pulses at different frequencies can be applied to measure the FID signal from different geometric regions within the materials to be analyzed. By measuring the FID signal from within different geometric regions during the waiting time, a plurality of different regions in the materials can be analyzed substantially in the same time span as needed to analyze a single geometric region within the materials. The method in the Granot '037 patent is not useful for well logging, however. First, using gradient pulses as needed for the Granot technique would dramatically increase the power consumption of the well logging instrument. Since the power carrying capacity of the well logging cable is limited, it is not preferred to have additional uses of power in the well logging instrument such as energizing gradient coils. Second, the method in the Granot '037 patent is intended primarily for measurements of the FID signal, rather than measurements of spin echo amplitude decay and $T_2$ as is more typical of well logging techniques. Using momentary gradient fields superimposed on the static magnetic field would make it difficult to measure spin echo amplitude decay and $T_2$ since the polarized nuclei in earth formations in any spatial volume would not have an opportunity to return to magnetic equilibrium between successive measurements made according to the technique disclosed in the Granot '037 patent.

SUMMARY OF THE INVENTION

The invention is a method for determining the nuclear magnetic resonance longitudinal relaxation time ($T_1$) of a medium. The method includes magnetically polarizing nuclei in the medium along a static magnetic field. The nuclei are momentarily inverted as to their magnetic polarization within each one of a plurality of different spatial volumes within the medium. The inversion is performed by transmitting a series of 180° pulses each at a frequency corresponding to the static magnetic field strength within each sensitive volume. The nuclei in each sensitive volume are then transversely magnetized after an individual recovery time corresponding to each one of the spatial volumes. An amplitude of a magnetic resonance signal from each one of the spatial volumes is measured in order to calculate the $T_1$ relaxation curve. In the preferred embodiment of the invention, the transverse magnetization is induced in each one of the individual sensitive volumes by transmitting radio frequency pulses at frequencies corresponding to the static magnetic field strength within each sensitive volume. In the preferred embodiment, the transverse magnetization is performed by transmitting a series of CPMG "read-out" pulse sequences, each sequence transmitted at a frequency corresponding to each one of the sensitive volumes and including measuring the amplitude of the resulting spin echoes in each CPMG sequence.

In another aspect of the invention, the transverse relaxation time distribution of the medium can be measured with an improved signal-to-noise ratio. The medium is polarized along a static magnetic field. A first CPMG echo train is acquired from within a first sensitive volume. The first CPMG train has an inter-echo spacing and a duration large enough to determine the presence of slowly relaxing components in the medium. Then a plurality of additional CPMG echo trains is acquired. Each of the additional echo trains corresponds to a different sensitive volume, and each of the additional CPMG echo trains has an inter-echo spacing and a duration less than the duration and echo spacing of the first CPMG echo train. Different sensitive volumes are measured by transmitting each additional CPMG sequence at a different radio frequency. In the preferred embodiment, the additional echo trains have a duration and inter echo spacing adapted to determine the presence of components in the formation having a transverse relaxation time less than about 33 milliseconds. The total duration of all the additional echo trains is about equal to the duration of the first echo train. In the preferred embodiment, the total radio frequency power transmitted in the all the additional echo trains is approximately equal to the radio frequency power transmitted in the first echo train.

DESCRIPTION OF THE PREFERRED EMBODIMENT

An NMR well logging apparatus which is suitable for use with this invention is described, for example, in U.S. patent application Ser. No. 08/606,089 filed on Feb. 23, 1996 entitled "NMR Apparatus and Method". The apparatus described in the Ser. No. 08/606,089 patent application includes a magnet for inducing a static magnetic field in the earth formations. The static magnetic field includes an amplitude gradient directed radially inwardly towards the longitudinal axis of the instrument. The apparatus disclosed in the Ser. No. 08/606,089 application includes an antenna through which pulses of RF power are conducted to excite nuclei of the earth formations surrounding the instrument. The antenna includes a wire coil wound around a high magnetic permeability ferrite. The ferrite includes a frequency control coil wound thereon. By passing a selectively controllable DC voltage through the frequency control coil, the tuning frequency of the antenna can be selectively controlled, making transmission and reception of RF energy at. The apparatus disclosed in the Ser. No. 08/606,089 patent application can make NMR measurements at a plurality of different frequencies. Since the static magnetic field imparted by the magnet disclosed in the Ser. No. 08/606,089 patent application includes an amplitude gradient, conducting NMR measurements at different frequencies will result in these different frequency NMR measurements taking place in different sensitive (excitation) volumes.

It is to be clearly understood that the apparatus disclosed in the Ser. No. 08/606,089 patent application is not the only apparatus which can be used for this invention. For purposes of this invention it is only necessary that the NMR apparatus be able to selectively excite different sensitive volumes to nuclear magnetic resonance, and selectively receive NMR signals from each of the selectively excited sensitive volumes. Using multiple frequencies for individual NMR measurement sequences in a gradient static magnetic field is a particularly convenient means by which to carry out the method of this invention, and so the apparatus disclosed in the Ser. No. 08/606,089 patent application is a particularly convenient instrument, but not the exclusive instrument by which to carry out the method of this invention.

Figure 1:
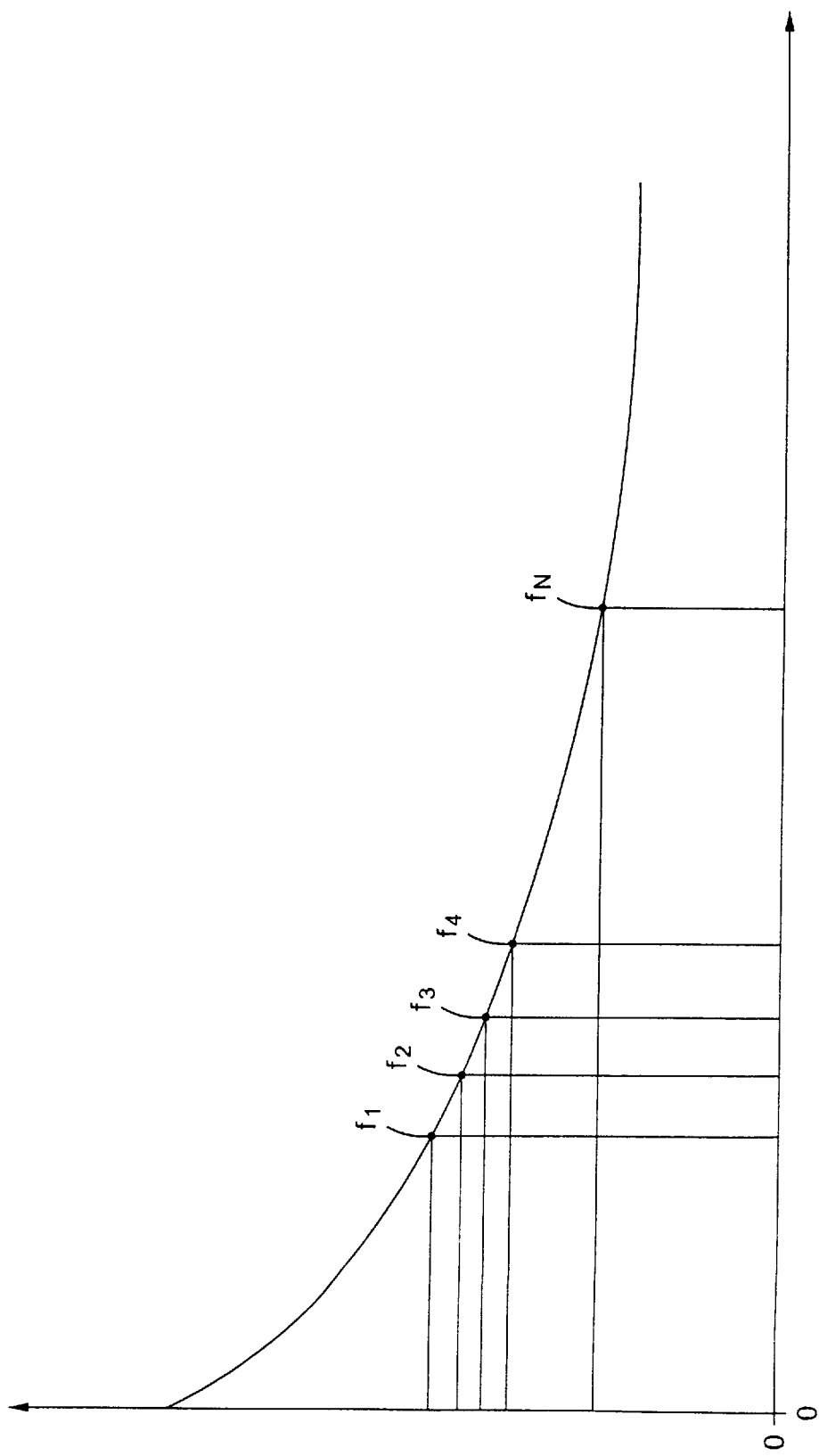
FIG. 1 shows a graph of amplitude of the static magnetic field of the magnet in an NMR well logging apparatus used with the invention.

FIG. 1 shows a graph of the amplitude of the static magnetic field, with respect to distance from the magnet, for the well logging apparatus described in the Ser. No. 08/606,089 patent application. The amplitude of the static magnetic field generally decreases with respect to the lateral distance from the magnet. As is well known in the art, nuclear magnetic resonance conditions occur when a radio frequency magnetic field is applied to materials polarized along a static magnetic field where the frequency of the RF magnetic field matches the product of the static magnetic field strength and the gyromagnetic ratio of the nuclei being polarized by the static magnetic field, this product being referred to as the Larmor frequency. As can be inferred from the graph in FIG. 1, by adjusting the frequency of the RF magnetic field, the distance from the magnet at which nuclear magnetic resonance conditions occur can be changed corresponding to the static magnetic field amplitude at that particular distance from the magnet. For example, if frequency $f_1$ is the highest frequency, resonance will occur at the smallest distance to the magnet, and so on through lower frequencies $f_2$ through $f_N$. Because nuclear magnetic resonance only occurs where the static magnetic field strength matches the RF magnetic field frequency, nuclear magnetic resonance measurements can be conducted within a number of different non-overlapping sensitive volumes by inducing nuclear magnetic resonance at different frequencies. A particular set of non-overlapping sensitive volumes which would result when using the apparatus described in the Ser. No. 08/606,089 patent application, for example, would comprise thin annular cylinders each having an average radius corresponding to the particular static magnetic field amplitude in which nuclear magnetic resonance would occur at a particular RF magnetic field frequency. The thickness of each annular cylinder would be related to the bandwidth of a receiver circuit in the NMR instrument and the rate at which the static magnetic field changes in amplitude.

This feature of the static magnetic field, and the selectable frequency capability for the RF magnetic field in the apparatus described in the Ser. No. 08/606,089 patent application makes it possible to conduct time-overlapping NMR measurements within different sensitive volumes. By time-overlapping NMR experiments in different sensitive volumes, it is possible to more efficiently use the RF transmitting components in the apparatus. The manner in which the RF transmitting components are used more efficiently will now be explained.

1. A Multiple Frequency CPMG Pulse Sequence for Improved SNR in Transverse Relaxation Time Measurement Nuclear magnetic transverse relaxation properties of materials are typically measured using Carr-Purcell-Meiboom-Gill ("CPMG") pulse sequences. For NMR relaxometry of fluids in the pore spaces of a porous medium, the CPMG sequences should include a sufficient number of 180° rephasing pulses to acquire substantially the entire relaxation spectrum. This means that the CPMG pulse sequence should usually extend about to the five times longest expected transverse relaxation time. The transverse relaxation spectrum is typically sampled at the maximum possible pulsing rate in order not to lose any pulse echoes whose amplitudes are related to fast relaxing (short $T_2$) components in the porous medium. The maximum rate corresponds to the minimum, or shortest, interecho time (TE) value of which the particular NMR instrument is capable. However, the data acquired using the shortest TE may be redundant for acquiring information related to the slower relaxing components of earth formations. It is known in the art to use this redundancy for SNR improvement by summing the measured spin-echo amplitudes over a number of predetermined time intervals or by using singular value decomposition ("SVD") analysis.

The method of applying RF pulses according to this invention can be better understood by comparing the following two NMR pulsing sequences, which have approximately equal average power consumption. The first such pulsing sequence is a polarity-alternated CPMG pulse sequence pair (referred to as a phase alternate pair sequence ("PAPS")). PAPS sequences are known in the art and can be described by the following expression:

$$90°_{\pm x} - \tau - (180°_y - 2\tau)_I - T_r$$

where I represents the number of 180° rephasing pulses (equal to the number of echoes in the CPMG echo train), $T_r$ represents the wait (repolarizing) time, and $\tau$ represents the Carr-Purcell spacing, which is equal to about ½ TE.

Figure 2:
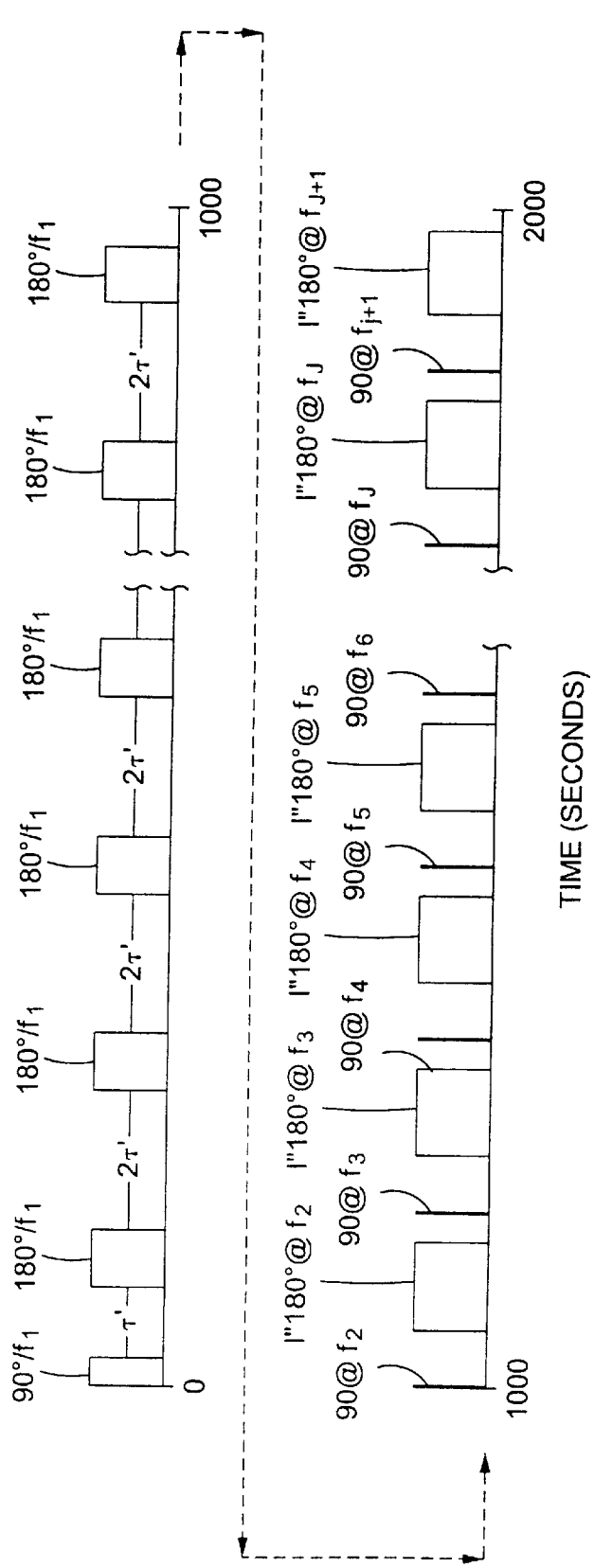
FIG. 2 shows a timing diagram for radio frequency power pulses generated by the NMR well logging apparatus in the method of the invention used to measure the transverse relaxation time of earth formations.

The NMR measurement sequence of this invention, however, is optimized by individually exciting nuclear magnetic resonance within a quantity, J+1, of different sensitive volumes during one complete measurement cycle. This measurement sequence is performed according as follows. Referring now to FIG. 2, an initial PAPS measurement sequence can be used to excite nuclei within a first sensitive volume using a Carr-Purcell spacing represented by τ' and a number of 180° rephasing pulses represented by I', as in the following expression:

$$90°_{\pm x} - \tau'(180°-2\tau')_{I'} - T_r$$

For clarity of the illustration in FIG. 2, only the first half of each PAPS sequence is shown in FIG. 2. The initial sequence is shown in FIG. 2 by a 90° pulse at frequency $f_1$ followed by a waiting period equal to τ'. After the waiting period, a series, numbering I', of 180° rephasing pulses at frequency $f_1$, each separated by waiting period 2τ', is applied to the antenna. (Not shown in the timing diagram of FIG. 2 is the inverse phase measurement set corresponding to the measurement set just described forming the second half of the PAPS measurement sequence.) The initial PAPS measurement sequence is intended to measure the relaxation characteristics of the components of the earth formations which have relatively long transverse relaxation times. In the initial PAPS measurement sequence, the TE can be relatively long (for example 2–4 msec, with an upper limit related to the magnitude of any gradient in the static magnetic field to avoid diffusion-related effects on the NMR signals) to minimize the total number of pulses generated, thereby minimizing the amount of power consumed in generating the pulses in the initial PAPS measurement sequence.

The initial PAPS measurement sequence can then be followed by a series of additional PAPS measurement sequences. These additional PAPS measurement sequences are used to excite nuclear magnetic resonance within a number, J, of additional sensitive volumes according to the following expression:

$$(90°_{\pm x} - \tau - (180° - 2\tau)_{I''} - T_r)_j; j=1, 2, 3, \ldots, J$$

where $I' = I\tau/\tau'$, $J \approx (I-I')/I''$, and $I''$ is selected to minimize the relative error for calculating the petrophysical parameters. To excite the J+1 sensitive volumes using the NMR well logging apparatus described in U.S. patent application Ser. No. 08/606,089, for example, a set of J+1 individual operating frequencies can be used, each of which corresponds to one of J+1 static magnetic field amplitudes located within in J+1 different spatial volumes within the earth formation.

The timing of the additional pulse sequences is shown in the lower portion of the timing diagram in FIG. 2. A 90° pulse at frequency $f_2$ is transmitted. After a waiting time $\tau''$, a shortened set, numbering $I''$, of 180° rephasing pulses is applied at this same frequency $f_2$. This procedure can be repeated, almost immediately after the end of the pulse sequence transmitted at frequency $f_2$, by another additional pulse sequence transmitted at frequency $f_3$, and so on through a final additional pulse sequence transmitted at frequency $f_{j-1}$. Note that the total number of RF pulses for all of the J additional pulse sequences can be about equal to the amount of time used in the initial PAPS sequence.

The additional pulse sequences are intended to measure relaxation characteristics of components of the earth formations which have relatively short relaxation times (previously described as being less than about 33 msec). The TE of the additional PAPS pulse sequences is typically shorter than that of the initial PAPS sequence. Typically the TE of the additional pulse sequences should be about 0.5 msec or less, and it is contemplated that the TE can be as small as the particular well logging apparatus is capable of using (which for at least one instrument known in the art is about 0.2 msec). Because the components of the earth formation measured using the additional pulse sequences have short relaxation times, the pulse sequence duration, and correspondingly the total number of pulses in each additional sequence, can be much smaller than it is in the initial PAPS sequence. It is expected that since the $T_2$ of the formation components measured during the additional pulse sequences is typically less than about 33 msec, a total sequence length of about 50 msec for each of the additional pulse sequences will be sufficient to measure the short relaxation time formation components accurately. It should be noted, however, that the wait (recovery) time between individual measurement sequences, within each sensitive volume, is not substantially changed because only one NMR excitation pulse sequence occurs within each sensitive volume during each complete measurement cycle, because a complete measurement cycle includes one of the initial PAPS sequences and J additional pulse sequences.

The pulse sequence of the invention was compared with prior art pulse sequences to determine the amount of improvement in the accuracy of calculated petrophysical parameters for a particular amount of RF power in each type of pulse sequence, and for any particular amount of noise in the spin echo amplitude signals.

Figure 4:
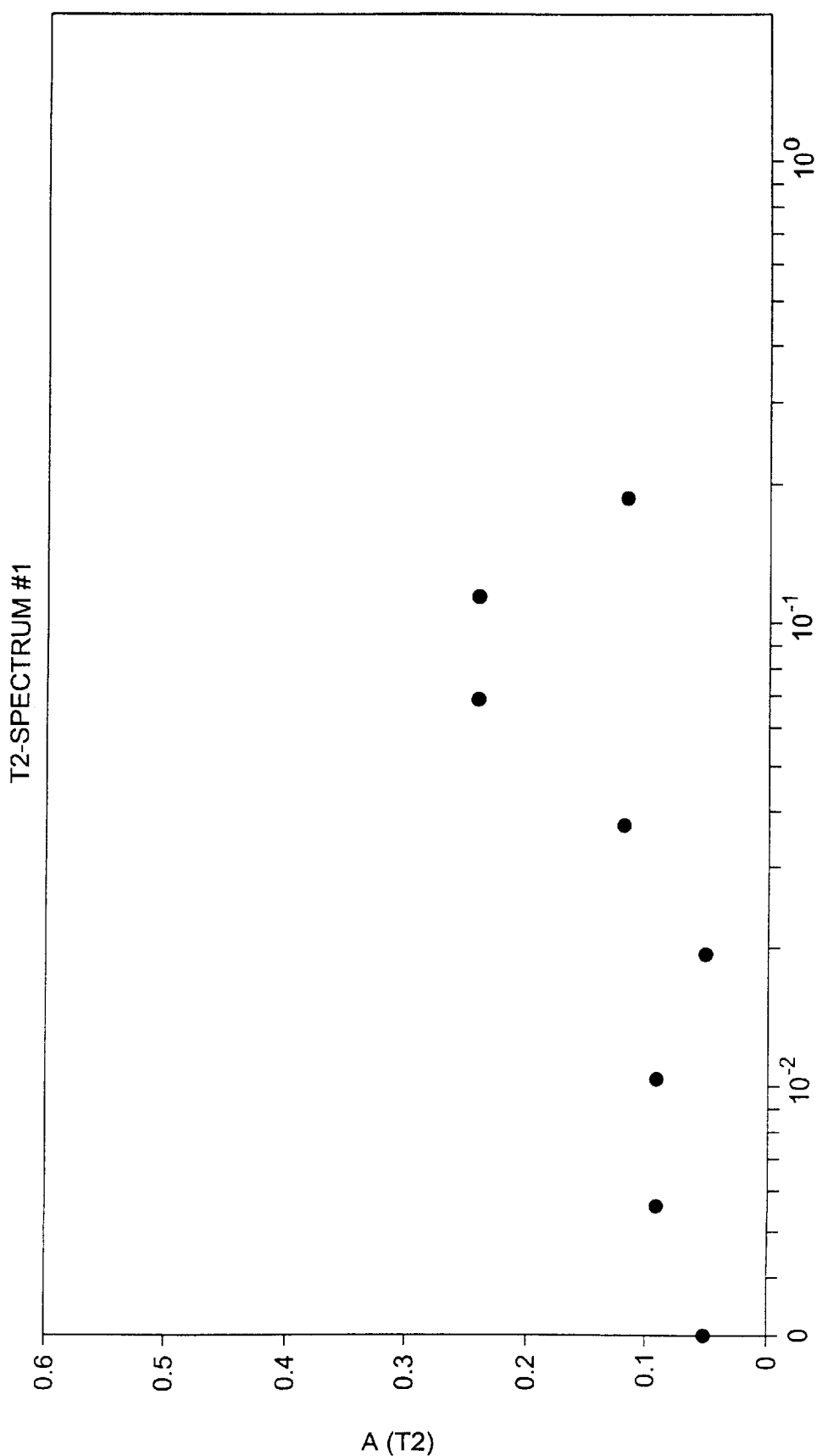
FIGS. 4–6 show example distributions of transverse relaxation time used to test the method of the invention.
Figure 5:
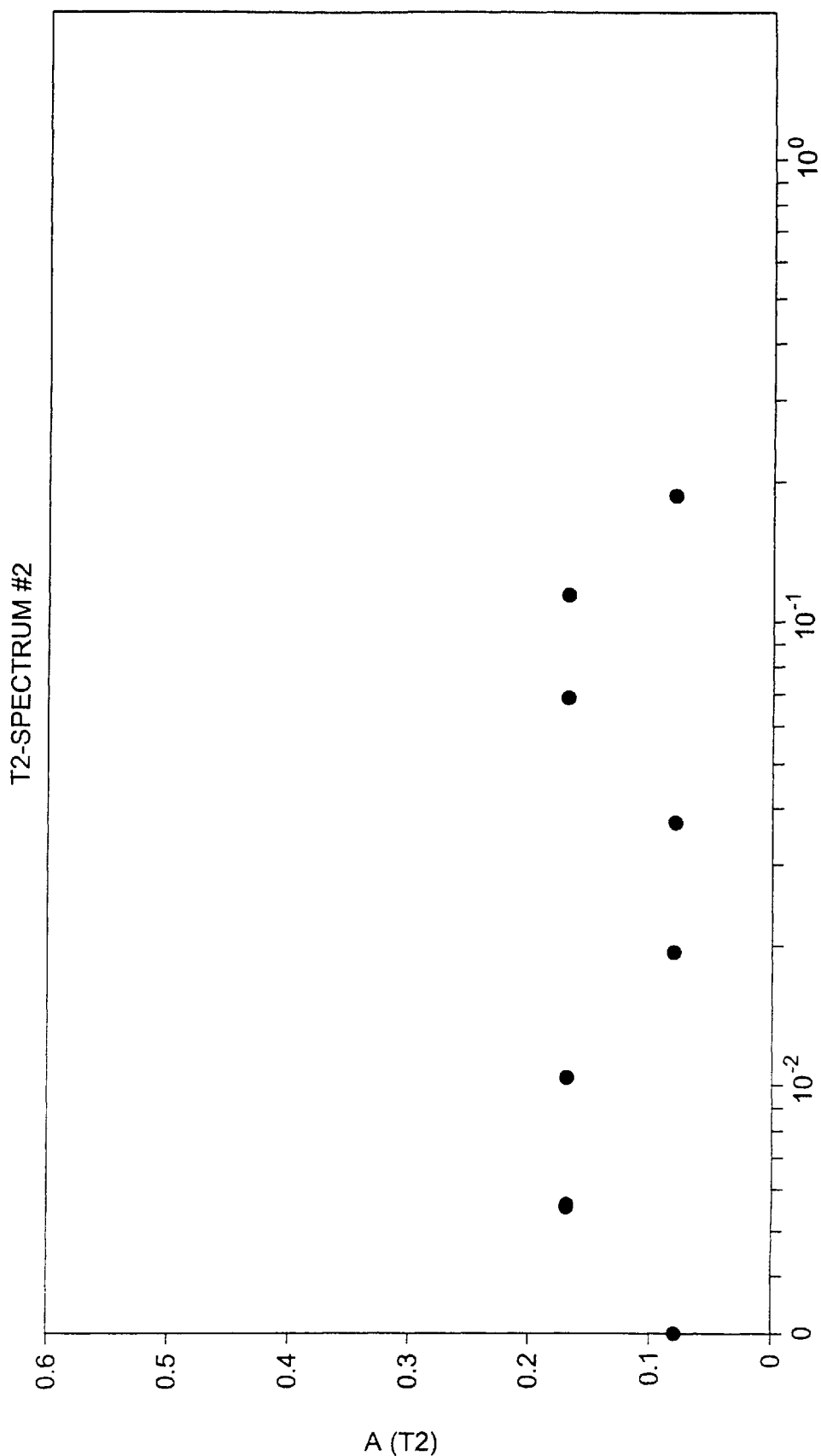
Figure 6:
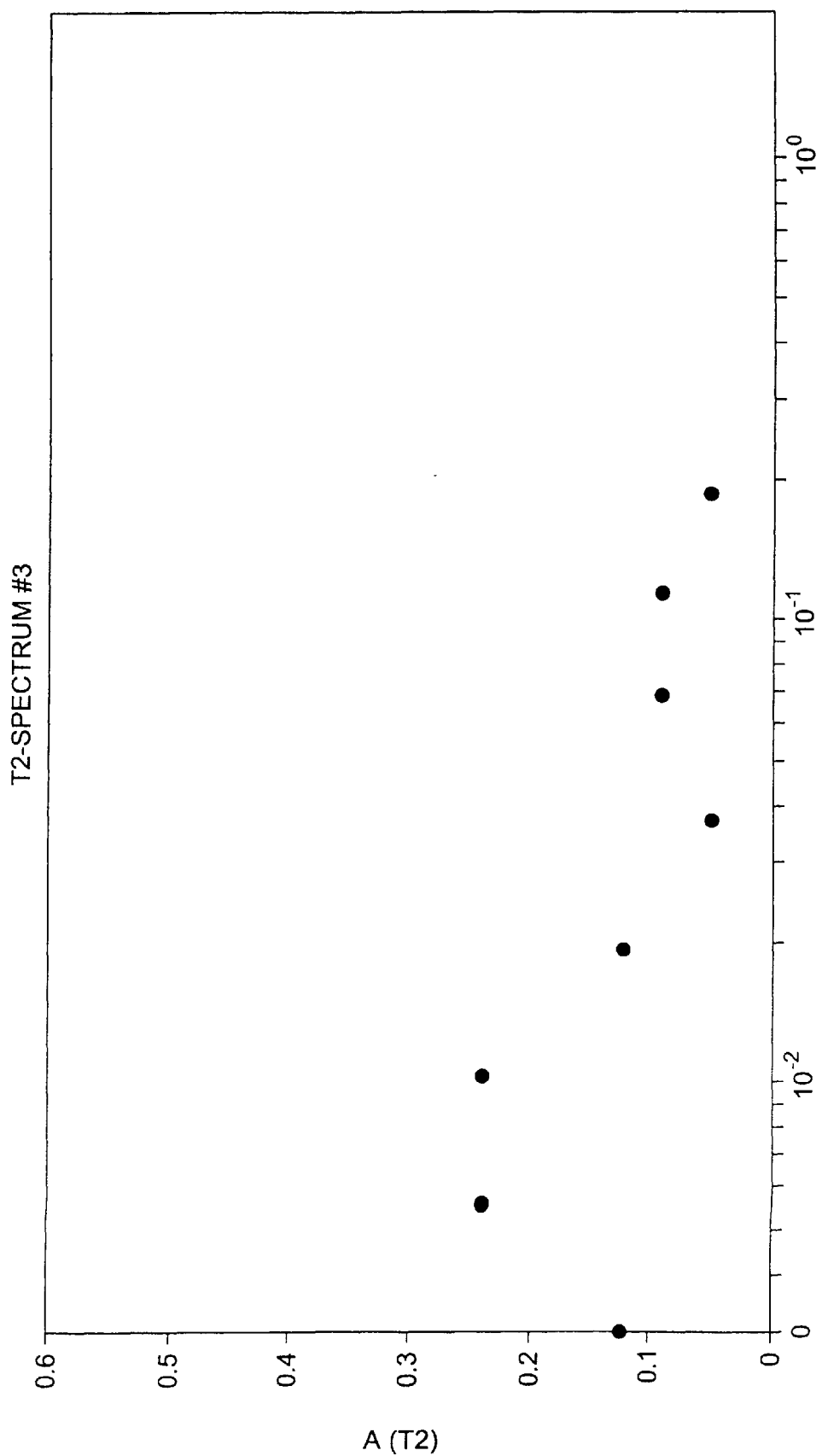

The first step in comparing the invention with prior art pulsing sequences is to generate a relaxation time distribution (also known as a spin echo amplitude decay curve) from sample $T_2$ distributions typical of earth formations. Typical $T_2$ relaxation distributions for earth formations extend from about 1 msec to about 200 msec and are bimodal in character. FIGS. 4 through 6 represent typical bimodal relaxation time distributions, denoted in several tables below as sample #1, sample #2 and sample #3, respectively. The example distribution of FIG. 4 includes a relatively large amount of "free" water and a relatively small amount of "bound" water. The distribution of FIG. 5 includes a more balanced mix of free and bound water, and the distribution of FIG. 6 includes a relatively large amount of bound water. As is known in the art, the bimodal distribution of the relaxation distribution of typical earth formations is related to the presence and relative fractional amounts of "free" water and "bound" water in the earth formations. The $T_2$ distributions shown in FIGS. 4–6 were used to generate corresponding relaxation time distributions (spin echo amplitude curves) by simple arithmetic calculation. The relaxation time distributions thus generated represent "noise free" spin echo amplitude signals, since they were calculated explicitly from known $T_2$ distributions.

The next step in comparing the invention to the prior art is to generate simulated "real" spin echo amplitude signals by stochastic simulation, or Monte Carlo modeling of noise. The "real" amplitude decay curve represents spin echo amplitude signals that would likely be measured by an actual NMR well logging instrument disposed in a medium having a $T_2$ distribution equal to the one used to generate the corresponding "noise free" spin echo amplitude decay curve. The simulated noise can be added to the "noise free" spin echo amplitude signals to generate synthetic pulse echo amplitude signals. The amount of noise added to the "noise free" amplitude signals can be selected by the system designer, and for convenience is described in the tables below according to the apparent signal to noise ratio ("SNR").

A set of synthetic "real" spin echo amplitude signals can be generated to correspond to each pulse sequence method to be compared, both prior art and by the method of this invention. Then the synthetic "real" spin echo amplitude signals can be analyzed according to well known multi-exponential techniques based on singular value decomposition and non-negative linear least squares to determine the apparent $T_2$ distribution of the "real" signals thus analyzed. The analysis techniques known in the art include determination of petrophysical parameters such as apparent porosity, which can be obtained by extrapolating the spin echo amplitude to a value which would obtain at a time to first echo of zero.

A plurality of different simulated "real" spin echo amplitude sets (each one having a different simulated "noise" set added to the noise-free spin echo amplitude set) were analyzed for each one of the $T_2$ distributions shown in FIGS. 4–6. The apparent porosity values calculated from each "real" spin echo amplitude set were statistically analyzed in terms of mean apparent porosity value and standard deviation of the apparent porosity value.

Below are tables comparing the results obtained using pulse sequences of the prior art to the pulse sequence of this invention. For the pulsing sequences according to the prior art the following parameters were chosen: TE=2τ=1 msec; I=1000. For the pulse sequence of the invention the following parameters were used: TE'=2τ'=2 msec; I'=500; TE=1 msec; I"=40; and J=12. Table 1 shows the comparative results for the $T_2$ distribution shown in FIG. 4, Table 2 shows the comparative results for the $T_2$ distribution shown in FIG. 5, and Table 3 shows the comparative results for the $T_2$ distribution shown in FIG. 6. The comparative results shown in each table represent a ratio of the standard deviation of the calculated porosity values with respect to the average value of porosity and represent the ratio of the standard deviation of the logarithmic mean of the $T_2$ distribution (represented by $T_{2LM}$) with respect to the average value of the logarithmic mean of the distribution. As is known in the art, higher accuracy of the result would correspond to a lower ratio.

TABLE 1

| | Prior Art Pulse Sequence | | Multiple-Frequency Pulse Sequence | |
|---|---|---|---|---|
| SNR | $\sigma(\phi_{nmr})/<\phi_{nmr}>$ | $\sigma(T_{2LM})/<T_{2LM}>$ | $\sigma(\phi_{nmr})/<\phi_{nmr}>$ | $\sigma(T_{2LM})/<T_{2LM}>$ |
| 10 | 0.090 | 0.255 | 0.044 | 0.146 |
| 20 | 0.056 | 0.165 | 0.024 | 0.072 |
| 50 | 0.024 | 0.081 | 0.013 | 0.043 |

TABLE 2

| | Prior Art Pulse Sequence | | Multiple-Frequency Pulse Sequence | |
|---|---|---|---|---|
| SNR | $\sigma(\phi_{nmr})/<\phi_{nmr}>$ | $\sigma(T_{2LM})/<T_{2LM}>$ | $\sigma(\phi_{nmr})/<\phi_{nmr}>$ | $\sigma(T_{2LM})/<T_{2LM}>$ |
| 10 | 0.082 | 0.241 | 0.047 | 0.137 |
| 20 | 0.054 | 0.153 | 0.024 | 0.066 |
| 50 | 0.029 | 0.077 | 0.014 | 0.04 |

TABLE 3

| | Prior Art Pulse Sequence | | Multiple-Frequency Pulse Sequence | |
|---|---|---|---|---|
| SNR | $\sigma(\phi_{nmr})/<\phi_{nmr}>$ | $\sigma(T_{2LM})/<T_{2LM}>$ | $\sigma(\phi_{nmr})/<\phi_{nmr}>$ | $\sigma(T_{2LM})/<T_{2LM}>$ |
| 10 | 0.092 | 0.206 | 0.079 | 0.172 |
| 20 | 0.063 | 0.146 | 0.029 | 0.074 |
| 50 | 0.029 | 0.072 | 0.015 | 0.039 |

The SNR (signal to noise ratio) is defined as: [total amplitude/standard deviation of the noise].

Improvements in the calculation of the apparent permeability using the pulse sequence method of the invention can also be obtained. For example, a method of calculating permeability from NMR data called the "SDR" method defines permeability in terms of NMR porosity and $T_{2LM}$ by the following relationship:

$$K_{nmr} \phi_{nmr}^4 T_{2LM}^2$$

See for example, C. E. Morriss et al, *Operating Guide for the Combinable Magnetic Resonance Tool*. The Log Analyst, November–December 1996, Society of Professional Well Log Analysts, Houston, Tex. The relative error of permeability can be defined by the expression:

$$\sigma(K_{nmr})/<K_{nmr}>=4\sigma(\phi_{nmr})/<\phi_{nmr}>+2\sigma(T_{2LM})/<T_{2LM}>$$

A comparison table for $K_{nmr}$ is shown below:

TABLE 4

| SNR | Prior Art Pulse Sequence $\sigma(K_{nmr})/<K_{nmr}>$ | Multiple Frequency Pulse Sequence $\sigma(K_{nmr})/<K_{nmr}>$ |
|---|---|---|
| 10 | 0.810 | 0.462 |
| 20 | 0.522 | 0.228 |
| 50 | 0.276 | 0.150 |

Also presented below in Table 5 is a comparison with respect to prior art techniques of the relative permeability error for different pulsing techniques according to the method of this invention each having approximately the same total RF energy content. The parameters for each pulse sequence (numbered 1 through 5 below) are as follows:

1) TE'=2τ'=2ms;  I'=500  TE=1ms  I"=20   J=24  SNR=20
2) TE'=2τ'=2ms;  I'=500  TE=1ms  I"=40   J=12  SNR=20
3) TE'=2τ'=2ms;  I'=500  TE=1ms  I"=80   J=6   SNR=20
4) TE'=2τ'=2ms;  I'=500  TE=1ms  I"=120  J=4   SNR=20
5) Prior Art CPMG:  I=1000  TE=1ms            SNR=20

TABLE 5

| Pulse sequence: | 1 | 2 | 3 | 4 | 5 (prior art) |
|---|---|---|---|---|---|
| Sample #1 $\sigma(K_{nmr})/<K_{nmr}>$ | 0.23 | 0.21 | 0.29 | 0.35 | 0.52 |
| Sample #2 $\sigma(K_{nmr})/<K_{nmr}>$ | 0.24 | 0.24 | 0.23 | 0.31 | 0.55 |
| Sample #3 $\sigma(K_{nmr})/<K_{nmr}>$ | 0.28 | 0.26 | 0.26 | 0.36 | 0.54 |

It can be concluded from the results shown in Table 5 that $\sigma(K_{nmr})/<K_{nmr}>$ is substantially insensitive to the value of I" within a range of about 20–80 and, correspondingly, J being within a range of about 24–6. The expected accuracy using sequence of the invention is about twice that using the pulse sequences known in the art where both types of pulse sequence have about the same total RF energy.

2. $T_1$ Measurement Using Multiple Frequency Pulsing

Pulse-echo techniques known in the art for measuring NMR longitudinal relaxation time ($T_1$) include inversion recovery ("IR") and saturation recovery ("SR"). In the IR technique, after polarization of the nuclei along the static magnetic field, a 180° RF pulse is applied to the instrument's antenna, causing inversion of the nuclear spin system within the sensitive volume. The 180° pulse is followed by a recovery time $R_i$, which is typically some predetermined value within the range of 0.05 to 5 times the expected value of $T_1$. Then a 90° "read-out" pulse is applied to the antenna. The amplitude of the free induction decay ("FID") following the 90° read-out pulse is measured. This amplitude measurement forms one point on a $T_1$ relaxation "curve". The relaxation curve represents a relationship of the FID amplitude with respect to the recovery time $R_1$. Typically the relaxation curve is determined by measuring FID amplitudes at a number of different predetermined recovery times. The relaxation curve can be used to determine the relaxation time $T_1$, as is known in the art.

After the first read-out pulse and measurement of the FID amplitude, the nuclear spin system is then allowed to return to equilibrium (alignment with the static magnetic field) by waiting for a time period, W. W is approximately equal to 5 times $T_1$. Then another point of the $T_1$ relaxation curve can be measured by again applying a 180° pulse, waiting for a different recovery time $R_2$, applying another 90° read-out pulse and measuring the FID amplitude. An expression for the relaxation in inversion recovery type measurements is:

$$M(R_i)=M_0-2M_0\exp(-R_i/T_1); i=1,2,\ldots,N$$

Transmitting an IR pulse sequence to make $T_1$ measurements is very time consuming, since an acquisition of just one point along the $T_1$ relaxation curve requires a time span of about $R_i+W>5(T_1)$.

The saturation recovery ("SR") technique is much less time consuming. The nuclear spin system is initialized quickly using several 90° pulses (called preparation pulses), to reduce the bulk magnetization of the nuclei to zero, and then the nuclear spin system is allowed to recover for a predetermined length of time before applying a read-out pulse. Since the initial condition (zero magnetization) is provided by the 90° pulses, no waiting time is required for reorientation with the static magnetic field. Thus an i-th point on the $T_1$ relaxation curve is acquired in a time interval of about $R_i$. An expression for relaxation in SR type measurements is as follows:

$$M(R_i)=M_0[1-\exp(R_i/T_1)]$$

Since in the IR technique the relaxation starts from bulk nuclear magnetization equal to $-M_0$, the range of magnetization is $2M_0$, as compared to a range of $M_0$ in the case of the SR technique. IR measurements therefore typically result in higher signal-to-noise ratio, assuming that the $T_1$ relaxation curve is acquired during the same time interval as it is for the SR type measurement.

Both techniques can use CPMG pulse sequences as a substitute for the 90° read-out pulses. Since $T_2$ information from the CPMG sequence is not needed in order to measure $T_1$, only the sum of the echoes in each CPMG sequence can be measured in order to increase the overall signal-to-noise ratio. In any event, IR/CPMG and SR/CPMG techniques are relatively time consuming to perform and so have not been used extensively in well logging applications.

Figure 3:
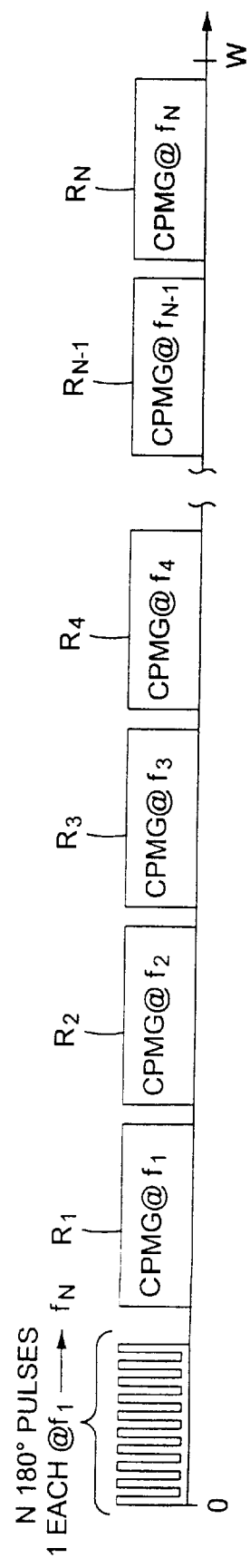
FIG. 3 shows a timing diagram for radio frequency power pulses used to measure longitudinal relaxation time of the earth formations.

Using the multiple frequency measurement system described in the invention, however, it is possible to provide a more time-efficient technique for measuring $T_1$, which can be described as follows. Referring now to FIG. 3, a plurality of different sensitive volumes prepolarized along a static magnetic field are inversely polarized in rapid succession. The inverse polarizations are performed by transmitting, in rapid succession, a series of ("inverting") 180° RF pulses at frequencies each corresponding to the static magnetic field amplitude in one of the sensitive volumes. This is shown in FIG. 3 as a number, N, of 180° "inversion" pulses, one pulse at each of frequencies $f_1$ through $f_N$. There need be virtually no waiting time between inverse polarization pulses for each one of the individual sensitive volumes because there is substantially no nuclear magnetic interaction between the sensitive volumes. The minimum time delay between each inverse polarization pulse is practically limited, therefore, only by the rate at which the NMR logging instrument can transmit 180° pulses at different frequencies.

The 180° inversion pulses can then be followed by a first (shortest) recovery time $R_1$, after which a first "read-out" CPMG pulse sequence is transmitted, shown in FIG. 3 at CPMG@$f_1$, which has a duration $T_{tr}$. The first CPMG sequence is transmitted at the first frequency, which can be the same frequency as the first 180° inversion pulse. The amplitudes of the echoes in the first CPMG sequence are measured to determine the first "point" of the $T_1$ relaxation curve.

A second CPMG sequence can then be transmitted at the second frequency (shown at CPMG@$f_2$) after a second recovery time $R_2>R_1+T_{tr}$. A second "point" on $T_1$ relaxation curve is then acquired form the echo amplitude measurements of the second CPMG sequence, starting at $t=R_2$. After a third recovery time $R_3>R_2+T_{tr}$, a third CPMG sequence (shown at CPMG@$f_3$) can be transmitted at the third frequency. The third "point" on the $T_1$ relaxation curve can be acquired by measurement of the echo amplitudes in the third CPMG sequence.

The transmission of CPMG sequences can then be repeated, at each remaining frequency, for as many as the number of frequencies, N, originally transmitted as 180° inversion pulses. There will then be N points on the relaxation curve measured from N different excitation volumes. To acquire a complete $T_1$ relaxation curve, the last recovery time $R_N$ is preferably equal to approximately the waiting time W (as previously explained, about equal to 5 times $T_1$). The $T_1$ measurement sequence performed according to this method may be run substantially continuously, as suggested by the timing diagram of FIG. 3, since the first sensitive volume will have substantially reestablished its initial magnetization $M_0$ by the time of completion of measurement of the last (N-th) point of the $T_1$ curve. It is contemplated that about thirty frequencies (N=30) will provide sufficient sampling to accurately determine the $T_1$ relaxation curve.

Below is a comparison of the duration of $T_1$ relaxation curve acquisition experiments for using SR/CPMG of the prior art and the method of this invention. Considering logarithmic spaced points, advantageous:

$$R_i=R_1 2^i$$

Then an SR/CPMG sequence requires approximately (time required for each CPMG sequence is assumed to negligible):

$$T_{SR}=\sum_{i=1}^{N} R_1 2^i = R_1(2^{N+1}-1)$$

For the $T_1$ measurement pulse sequence of the invention, the sequence has N-1 measurement enclosed in the last and the longest $R_N$ interval, therefore:

$$T=R_N=R_1 2^N.$$

Note that an IR measurement sequence would require a time $T_{IR}=N R_1 (2^{N+1}-1)$, which is about 2N times more than the time needed for the pulse sequence according to the invention. A comparison of signal-to-noise ratio (SNR) between the invention and SR sequences per unit time can be expressed as:

$$SNR/SNR_{SR}=2(T_{SR}/T)^{1/2}\approx 2.8$$

The factor 2 appearing in the last equation is due to the magnetization range $2M_0$ in the sequence of the invention as opposed to the magnetization range $M_0$ for the SR/CPMG sequence known in the art.

It should be noted that the method for measuring $T_1$ disclosed herein is not limited to well logging applications. For example, $T_1$ measurement of core samples of the earth formations removed from the wellbore can be made much more efficient using the method of this invention. Other applications for $T_1$ can be similarly improved using the method of this invention.

Those skilled in the art will devise other embodiments of this invention which do not depart from the spirit of the invention disclosed herein. Accordingly, the scope of the invention should be limited only by the attached claims.

What is claimed is:

1. A method for determining nuclear magnetic resonance longitudinal relaxation time of a medium, comprising:

magnetically polarizing nuclei in said medium along a static magnetic field;

changing said magnetic polarization of said nuclei within each one of a plurality of different spatial volumes within said medium to a different state of magnetization;

transversely magnetizing said nuclei in each one of said spatial volumes after a different recovery time for each one of said spatial volumes; and measuring a magnetic resonance signal from each one of said spatial volumes.

2. The method as defined in claim 1 wherein said static magnetic field comprises a different amplitude within each one of said spatial volumes.

3. The method as defined in claim 2 wherein said step of changing said polarization further comprises transmitting radio frequency pulses at frequencies corresponding to the amplitude of said static magnetic field within each one of said spatial volumes.

4. The method as defined in claim 1 wherein said steps of transverse magnetizing and measuring said signal comprises CPMG pulse sequences.

5. The method of claim 1 wherein said different state of magnetization is selected from a group consisting of (i) rotated substantially 90° relative the static magnetic field, and, (ii) rotated substantially 180° relative to the static magnetic field.

* * * * *